(12) United States Patent
Liu et al.

(10) Patent No.: US 11,236,107 B2
(45) Date of Patent: Feb. 1, 2022

(54) CRYSTAL OF TRICYCLIC COMPOUND

(71) Applicant: Chia Tai Tianqing Pharmaceutical Group Co., Ltd., Lianyungang (CN)

(72) Inventors: Shilan Liu, Shanghai (CN); Dahai Wang, Shanghai (CN); Guibai Liang, Shanghai (CN); Honglin Wang, Shanghai (CN); Guoping Hu, Shanghai (CN); Jian Li, Shanghai (CN); Shuhui Chen, Shanghai (CN)

(73) Assignee: Chia Tai Tianqing Pharmaceutical Group Co., Ltd., Lianyungang (CN)

( * ) Notice: Subject to any disclaimer, the term of this patent is extended or adjusted under 35 U.S.C. 154(b) by 0 days.

(21) Appl. No.: 16/639,395

(22) PCT Filed: Aug. 17, 2018

(86) PCT No.: PCT/CN2018/100988
§ 371 (c)(1),
(2) Date: Feb. 14, 2020

(87) PCT Pub. No.: WO2019/034139
PCT Pub. Date: Feb. 21, 2019

(65) Prior Publication Data
US 2020/0255449 A1 Aug. 13, 2020

(30) Foreign Application Priority Data
Aug. 18, 2017 (CN) .......................... 201710714247.3

(51) Int. Cl.
*C07D 495/14* (2006.01)
*A61K 31/4188* (2006.01)
*A61P 37/00* (2006.01)

(52) U.S. Cl.
CPC ........ *C07D 495/14* (2013.01); *A61K 31/4188* (2013.01); *C07B 2200/13* (2013.01)

(58) Field of Classification Search
CPC .............. C07D 495/14; C07B 2200/13; A61K 31/4188; A61P 37/00
See application file for complete search history.

(56) References Cited

U.S. PATENT DOCUMENTS 9,260,434 B2  2/2016  Mautino

FOREIGN PATENT DOCUMENTS

| CN | 103547579 A | 1/2014 |
| CN | 105884828 A | 8/2016 |
| WO | WO 2016059412 A1 | 4/2016 |
| WO | WO 2017140274 A1 | 8/2017 |

OTHER PUBLICATIONS

Norris (Experimental Organic Chemistry, McGraw-Hill Book Company, Inc., 2nd Edition, 1-4) (Year: 2004).*
Morissette et al. (High-throughput crystallization: polymorphs, salts, co-crystals and solvates of pharmaceutical solids, Advanced Drug Delivery Reviews, 56, 275-300). 2003. (Year: 2003).*
Chinese Search Report in Chinese Patent Application No. CN 2018800533568, dated Jan. 29, 2021 (1 page).
International Search Report for PCT/CN2018/100988 dated Nov. 14, 2018.
Written Opinion of the International Searching Authority for PCT/CN2018/100988, dated Nov. 14, 2018.

* cited by examiner

*Primary Examiner* — Theodore R. Howell
(74) *Attorney, Agent, or Firm* — Nixon Peabody LLP

(57) ABSTRACT

The present application relates to a crystal of a tricyclic compound, in particular to a crystal of (S)-8-(4,4-difluorocyclohexyl)-8H-thieno[3,4]pyrrolo[1,5-a]imidazole, a preparation method therefor, a crystal composition and a pharmaceutical composition thereof and the use thereof. The X-ray powder diffraction spectrum of the crystal of the compound of formula I in the present application, represented by a 2θ value, has a diffraction peak at about 11.49°, 15.05°, 20.14°, 21.53° or 21.79°. The crystal of the compound of formula I in the present application has excellent physical properties, high safety and metabolic stability, and has a good inhibitory effect on IDO and a high medicinal value.

20 Claims, 2 Drawing Sheets

CRYSTAL OF TRICYCLIC COMPOUND

REFERENCES TO RELATED APPLICATIONS

This application is a U.S. national stage of PCT/CN2018/100988 filed on Aug. 17, 2018, which claims the benefits of the Chinese patent application No. 201710714247.3, filed on Aug. 18, 2017 before the National Intellectual Property Administration, P. R. China, the contents of which are all incorporated herein by reference in their entireties.

FIELD OF THE INVENTION

The present application belongs to the field of pharmaceutical technology, and relates to a crystal of a tricyclic compound, and more specifically to a crystal of (S)-8-(4,4-difluorocyclohexyl)-8H-thieno[3,4]pyrrolo[1,5-a]imidazole. This application also relates to a preparation method for the crystal of (S)-8-(4,4-difluorocyclohexyl)-8H-thieno[3,4]pyrrolo[1,5-a]imidazole, as well as a crystal composition, a pharmaceutical composition and use thereof.

BACKGROUND OF THE INVENTION

Tryptophan (Trp) is an essential amino acid required for the biosynthesis of proteins, nicotinic acid and neurotransmitter 5-hydroxytryptamine. Indoleamine 2,3-dioxygenase (also known as INDO or IDO) is an enzyme in the first rate-limiting step of catalyzing the degradation of L-tryptophan to N-formylkynurenine. In human cells, IFN-γ stimulation induces activation of IDO, which leads to a depletion of tryptophan, thereby arresting the growth of tryptophan-dependent cellular pathogens such as *Toxoplasma gondii* and *Chlamydia trachomatis*. IDO activity also has an anti-proliferative effect on many tumor cells, and IDO induction has been observed in vivo during rejection of allogeneic tumors, indicating a possible role for this enzyme in the tumor rejection process.

The existing IDO inhibitors are mainly divided into the following categories: 1) competitive inhibitors, such as tryptophan derivative 1-MT; 2) non-competitive inhibitors, such as phenylimidazole; 3) anti-competitive inhibitors, such as alkaloid exiguamine A; 4) inhibitors which act through other action mechanisms. These categories of inhibitors generally have problems such as low inhibitory efficiency, inability to penetrate cell membranes, and producing indole ring structure metabolites. In the 1990s, the derivative 1-methyltryptophan (1-MT), which is obtained through structural modification of tryptophan (a substrate of IDO) as a template, is commonly used IDO inhibitor in experiments in vivo and in vitro, with an inhibition constant (Ki) of 34 µM. Up to now, compound NLG919 from New Link Genetics in the United States and compound INCB024360 from Incyte in the United States have entered clinical trials.

With regard to an active compound with identified commercial use, the chemical stability, solid state stability, metabolic properties in vivo, and storage life of the active ingredient are all very important factors. Therefore, it is very important for drug production and storage to provide a drug with the above required properties.

SUMMARY OF THE INVENTION

A tricyclic compound represented by formula I, the chemical name of which is (S)-8-(4,4-difluorocyclohexyl)-8H-thieno[3,4]pyrrolo[1,5-a]imidazole, has a structural formula as follows:

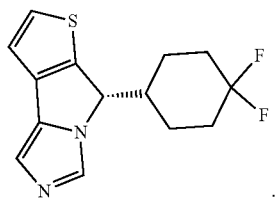

Formula I

In one aspect, the present application provides a crystal of the compound of formula I.

The crystal may be in the form of a non-solvate or a solvate, such as a hydrate.

The crystal of the compound of formula I has better IDO inhibitory activity and higher stability exhibited by the crystal, and therefore has higher medicinal value in terms of physical properties, safety and metabolic stability.

The crystal of the compound of formula I in the present application is characterized in that an X-ray powder diffraction spectrum thereof has diffraction peaks expressed by 2θ values at about 11.49°, 11.99°, 15.05°, 20.14°, 21.53°, or 21.79°; typically, the X-ray powder diffraction spectrum thereof has diffraction peaks expressed by 2θ values at about 11.49°, 11.99°, 15.05°, 17.99°, 18.24°, 19.44°, 20.14°, 21.53°, 21.79°, 25.09°, 27.20° or 28.00°; more typically, the X-ray powder diffraction spectrum thereof has diffraction peaks expressed by 2θ values at about 11.49°, 11.99°, 15.05°, 17.99°, 18.24°, 19.44°, 20.14°, 21.53°, 21.79°, 23.64°, 23.98°, 25.09°, 27.20°, 28.00°, 29.35°, 31.22°, 32.01°, 32.21°, 36.70° or 38.87°. More typically, the X-ray powder diffraction spectrum thereof has diffraction peaks expressed by 2θ values at about 11.49°, 11.99°, 13.89°, 15.05°, 17.99°, 18.24°, 19.44°, 20.14°, 21.02°, 21.53°, 21.79°, 23.64°, 23.98°, 25.09°, 25.64°, 26.84°, 27.20°, 28.00°, 28.46°, 29.35°, 31.22°, 32.01°, 32.21°, 32.89°, 34.18°, 35.02°, 35.81°, 36.70° or 38.87°.

In one embodiment of the present application, the peak positions and intensities of the characteristic peaks in the X-ray powder diffraction spectrum of the crystal of the compound of formula I in the present application have the characteristics shown in Table 1.

TABLE 1

| No. | 2θ (°) | Relative intensity (I/I$_0$) |
|---|---|---|
| 1 | 11.49 | 29.7 |
| 2 | 11.99 | 10.4 |
| 3 | 13.89 | 3.5 |
| 4 | 15.05 | 41.0 |
| 5 | 17.99 | 18.1 |
| 6 | 18.24 | 10.1 |
| 7 | 19.44 | 12.0 |
| 8 | 20.14 | 47.7 |
| 9 | 21.02 | 4.4 |
| 10 | 21.53 | 92.1 |
| 11 | 21.79 | 100.0 |
| 12 | 23.64 | 6.6 |
| 13 | 23.98 | 9.8 |
| 14 | 25.09 | 12.5 |
| 15 | 25.64 | 4.3 |
| 16 | 26.84 | 3.1 |
| 17 | 27.20 | 12.9 |
| 18 | 28.00 | 12.0 |
| 19 | 28.46 | 1.8 |
| 20 | 29.35 | 7.1 |
| 21 | 31.22 | 9.2 |
| 22 | 32.01 | 6.3 |
| 23 | 32.21 | 7.8 |

TABLE 1-continued

| No. | 2θ (°) | Relative intensity (I/I₀) |
|---|---|---|
| 24 | 32.89 | 4.9 |
| 25 | 34.18 | 3.0 |
| 26 | 35.02 | 1.2 |
| 27 | 35.81 | 2.0 |
| 28 | 36.70 | 5.3 |
| 29 | 38.87 | 7.2 |

In one embodiment of the present application, an X-ray powder diffraction spectrum of the crystal of the compound of formula I in the present application is shown in FIG. 1.

In one embodiment of the present application, a differential scanning calorimetry (DSC) diagram of the crystal of the compound of formula I in the present application has an absorption peak at about 207° C.

In one embodiment of the present application, a differential scanning calorimetry (DSC) diagram of the crystal of the compound of formula I in the present application is shown in FIG. 2.

In another aspect, the present application provides a crystal composition, wherein the crystal of the compound of formula I accounts for 50% or more, preferably 80% or more, more preferably 90% or more, and most preferably 95% or more by weight of the crystal composition. Other ingredients in the composition are amorphous forms, or other forms of crystals of the compound of formula I.

The present application provides a pharmaceutical composition, comprising a therapeutically effective amount of a crystal of the compound of formula I, or the above-mentioned crystal composition. The pharmaceutical composition may contain at least one pharmaceutically acceptable carrier or other vehicles. A pharmaceutically acceptable carrier can be a solid or a liquid. The solid carrier may include one or more substances of a flavoring agent, a lubricant, a solubilizer, a suspending agent, a filler, a binder, a tablet disintegrant, or an encapsulated material. Suitable solid carriers include, for example, magnesium stearate, talc, sucrose, lactose, dextrin, starch, gelatin, cellulose, methyl cellulose, sodium carboxymethyl cellulose, polyvinylpyrrolidone. Liquid carriers are used to prepare a composition such as solution, suspension, emulsion, syrup and the like. Suitable liquid carriers for oral and parenteral administration include water, alcohols, oils and the like.

The above pharmaceutical composition can be prepared into a certain dosage form, and the administration route is preferably oral administration, parenteral (including subcutaneous, intramuscular and intravenous) administration, rectal administration and the like. For example, dosage forms suitable for oral administration include tablet, capsule, granule, pulvis, pill, powder, lozenge, syrup or suspension; dosage forms suitable for parenteral administration include aqueous or nonaqueous injection solution or emulsion; dosage forms suitable for rectal administration include suppository using hydrophilic or hydrophobic carriers. According to the need, the above dosage forms can also be prepared into dosage forms suitable for rapid release, delayed release or controlled release of the active ingredient.

In another aspect, the present application provides use of the crystal of the compound of formula I, the above-mentioned crystal composition, or the above mentioned pharmaceutical composition in manufacture of a medicament for treating indoleamine 2,3-dioxygenase (IDO)-mediated immunosuppressive disease(s). The crystal of the compound of formula I, the above-mentioned crystal composition, or the above-mentioned pharmaceutical composition of the present application can be used alone or in combination with other medicaments, to manufacture a medicament for treating indoleamine 2,3-dioxygenase (IDO)-mediated immunosuppressive disease(s).

In another aspect, the present application provides a method for treating indoleamine 2,3-dioxygenase (IDO)-mediated immunosuppressive disease(s), comprising administering a therapeutically effective amount of the crystal of the compound of formula I, the above-mentioned crystal composition, or the above mentioned pharmaceutical composition to a mammal in need thereof. The mammal is preferably human.

In another aspect, the present application provides a crystal of the compound of formula I, the above-mentioned crystal composition, or the above-mentioned pharmaceutical composition for use in the treatment of indoleamine 2,3-dioxygenase (IDO)-mediated immunosuppressive disease(s).

The immunosuppressive disease is associated with infectious disease or cancer.

The infectious disease is selected from infections of the following viruses: influenza virus, hepatitis C virus (HCV), human papilloma virus (HPV), cytomegalovirus (CMV), polio virus, herpes zoster virus, human immunodeficiency virus (HIV), Epstein-Barr virus (EBV) or Coxsackie virus. The cancer is selected from colon cancer, pancreatic cancer, breast cancer, prostate cancer, lung cancer, brain cancer, ovarian cancer, cervical cancer, testicular cancer, kidney cancer, head or neck cancer, lymphoma, leukemia or melanoma.

In another aspect, the present application provides a method for preparing a crystal of the compound of formula I, comprising: (1) dissolving the compound of formula I in an organic solvent until solution being clear, which is filtered to remove insoluble substance; (2) concentrating the filtrate obtained in step (1) to a solid-liquid mixed state, producing a solid-liquid mixture which is dissolved by heating, stirred with refluxing for 1 to 2 hours, and cooled for crystallization.

In one embodiment of the method for preparing a crystal of the compound of formula I of the present application, the organic solvent in step (1) is one or more solvents selected from C1-C4 alcohols, nitriles, ketones, furans, and oxane solvents.

In one embodiment of the method for preparing a crystal of the compound of formula I of the present application, the organic solvent in step (1) is one solvent or a mixed solvent selected from methanol, ethanol, acetonitrile, acetone, butanone, tetrahydrofuran, and 1,4-dioxane; preferably methanol or ethanol.

In one embodiment of the method for preparing a crystal of the compound of formula I in the present application, a molar volume ratio of the compound of formula I to the organic solvent in step (1) is 1 mmol:5-10 mL; preferably 1 mmol:8-10 mL; further preferably 1 mmol:9-10 m L.

In one embodiment of the method for preparing a crystal of the compound of formula I of the present application, in step (2), when the filtrate is concentrated to a solid-liquid mixed state, a volume of the organic solvent in the solid-liquid mixture accounts for 15% to 30%, preferably 15% to 20% of a total volume of the organic solvent in step (1).

In one embodiment of the method for preparing a crystal of the compound of formula I of the present application, a temperature of the refluxing in step (2) is 50° C. to 80° C., preferably 65° C. to 80° C.

In one embodiment of the method for preparing a crystal of the compound of formula I of the present application, a temperature of cooling for crystallization in step (2) is 20° C. to 30° C., preferably 20° C. to 25° C.

In one embodiment of the present application, the above-mentioned method for preparing the crystal of the compound of formula I further comprises: (3) filtering; (4) drying.

In one embodiment of the method for preparing a crystal of the compound of formula I of the present application, conditions for the drying in step (4) comprise drying at normal temperature, drying under reduced pressure or air-blast drying, and preferably drying under reduced pressure. Equipment for drying is a fume hood, a vacuum oven or an air-blast oven, preferably a vacuum oven. The temperature for drying is 50° C. to 80° C., preferably 60° C. to 70° C.

In the present application, "crystal" refers to a solid having a highly regular chemical structure. The crystal in this application at least has a crystalline form in a specific weight percentage. The specific percentage is 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 10% and 99.9%. Preferably, the specific percentage is 50%, 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 50% and 99.9%. Further preferably, the specific percentage is 80%, 85%, 87%, 88%, 89%, 90%, 91%, 92%, 93%, 94%, 95%, 96%, 97%, 98%, 99%, 99.5%, 99.9%, or any percentage between 80% and 99.9%. Still further preferably, the specific percentage is 90%, 91%, 92%, 93%, 94%, 95%, 96%, 97%, 98%, 99%, 99.5%, 99.9%, or any percentage between 90% and 99.9%.

In this application, the X-ray powder diffraction spectrum of a sample is measured under the following conditions: instrument model: Bruker D8 Advance X-ray diffractometer (PDS-PF-XRD-01); test method: using approximately 10 to 20 mg samples for XRPD detection. The detailed XRPD parameters are as follows: light tube: Cu, Kα, ($\lambda$=1.54056 Å); light tube voltage: 40 kV, light tube current: 40 mA; divergence slit: 0.60 mm; detector slit: 10.50 mm; anti-scatter slit: 7.10 mm; scanning range: 4°-40°; step diameter: 0.02°; step length: 0.12 seconds; sample disc rotation speed: 15 rpm.

In this application, a DSC spectrum is measured under the following conditions: instrument: Q2000 DSC Differential Scanning calorimeter (PDS-PF-DSC-02); temperature range: 30° C. to 300° C.; heating rate: 10° C./min.

It should be noted that, in an X-ray powder diffraction spectrum, a diffraction pattern obtained from a crystal compound is usually characteristic for a specific crystal form. Wherein, relative intensities of bands (especially at low angles) can vary depending upon preferential orientation effects resulting from the differences of crystal conditions, particle sizes, and other measuring conditions. Therefore, the relative intensities of diffraction peaks are not characteristic for the aimed crystal form. It is the relative positions of peaks rather than relative intensities thereof that should be paid more attention when judging whether a crystal form is the same as a known crystal form. In addition, for any given crystal form, there may be a slight error in the positions of peaks, which is also well known in the field of crystallography. For example, the position of a peak may shift due to the change of a temperature, the movement of a sample or the calibration of an instrument and so on when analyzing the sample, and the measurement error of 2θ value is sometimes about ±0.2°. Accordingly, this error should be taken into consideration when determining each crystalline structure. Usually, the position of a peak is expressed by 2θ angle or interplanar spacing d in an XRD pattern, and there is a simple conversion relationship therebetween: d=$\lambda$/2 sin θ, wherein d represents the interplanar spacing, $\lambda$ represents the wavelength of incident X-ray, and θ represents the diffraction angle. For the same crystal form of the same compound, the positions of peaks in XRD spectra thereof have similarity as a whole, and the errors of relative intensities may be larger. It should also be pointed out that due to factors such as reduced contents, parts of diffraction lines may be absent during the identification of a mixture. At this time, even one band may be characteristic for a given crystal, without depending upon all the bands observed in a high purity sample.

DSC is used to measure a transition temperature when a crystal absorbs or releases heat due to the change of the crystal structure thereof or the crystal melting. For the same crystal form of the same compound, during a continuous analysis, the error of a thermal transition temperature and a melting point is typically within about 5° C., usually within about 3° C. When it is said that a compound has a given DSC peak or melting point, it means that the DSC peak or melting point is varied ±5° C. DSC provides an auxiliary method to distinguish different crystal forms. Different crystal morphologies can be identified based on different transition temperature characteristics thereof. It should be pointed out that for mixtures, the DSC peak or melting point thereof may vary within a larger range. In addition, since the melting process of the substance is accompanied by the decomposition, the melting temperature is related to the heating rate.

Definition

When used in the Description and the appended claims of the present application, unless indicated to the contrary, the following terms shall have the indicated meanings.

"Mammal" includes human; domestic animal, such as laboratory mammal; domestic pet (such as cat, dog, pig, caprinae, cattle, sheep, goat, horse, or rabbit); and non-domestic mammal, such as wild mammal and the like.

The term "pharmaceutical composition" refers to a formulation of a compound of the present application and a medium generally accepted in the art for delivering a bioactive compound to a mammal, such as human. The medium comprises all pharmaceutically acceptable carriers for its use. A pharmaceutical composition facilitates administration of a compound to an organism.

The term "therapeutically effective amount" refers to the amount of a medicament or drug which is non-toxic but sufficient to achieve the expected effect. The effective amount may be determined individually, and depends on the age and general condition of the subject as well as the specific active substance. The effective amount in specific case can be determined by a person skilled in the art through conventional test.

In the present application, "pharmaceutically acceptable carrier" refers to those carriers which are administered together with active ingredient, have no apparent irritation and will not impair the bioactivity and property of the active compound. Other information regarding the carriers may be referred to Remington: The Science and Practice of Pharmacy, 21st Ed., Lippincott, Williams & Wilkins (2005), the contents of which are incorporated herein by reference.

In the present application, "molar ratio" and "mole ratio" are equivalent to each other. In the present application, "room temperature" means 20° C. to 25° C.

DETAILED DESCRIPTION OF THE INVENTION

Figure 1:
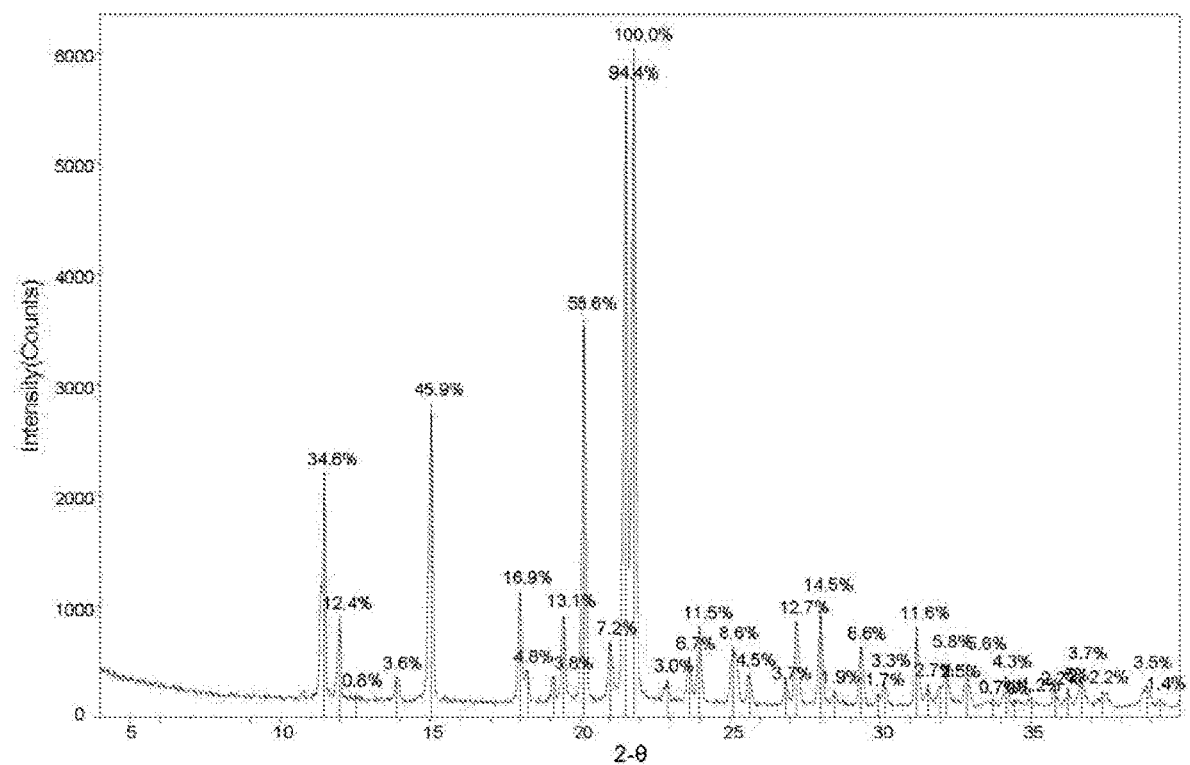
FIG. 1 is an X-ray powder diffraction pattern (XRPD) of the crystal in Example 2.
Figure 2:
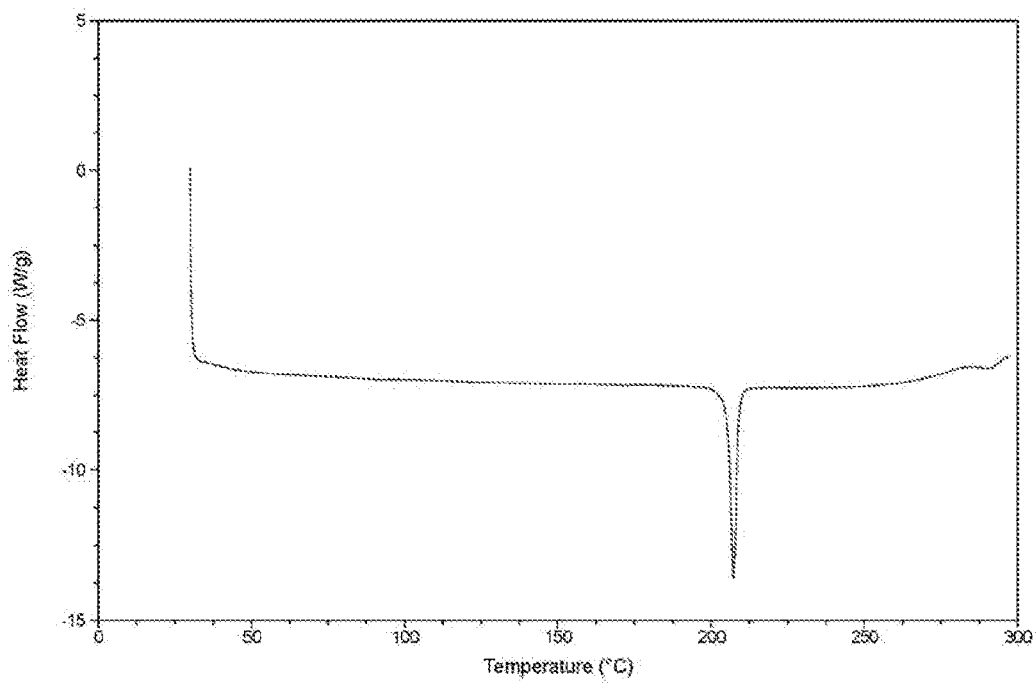
FIG. 2 is a differential scanning calorimetry (DSC) curve of the crystal in Example 2.
Figure 3:
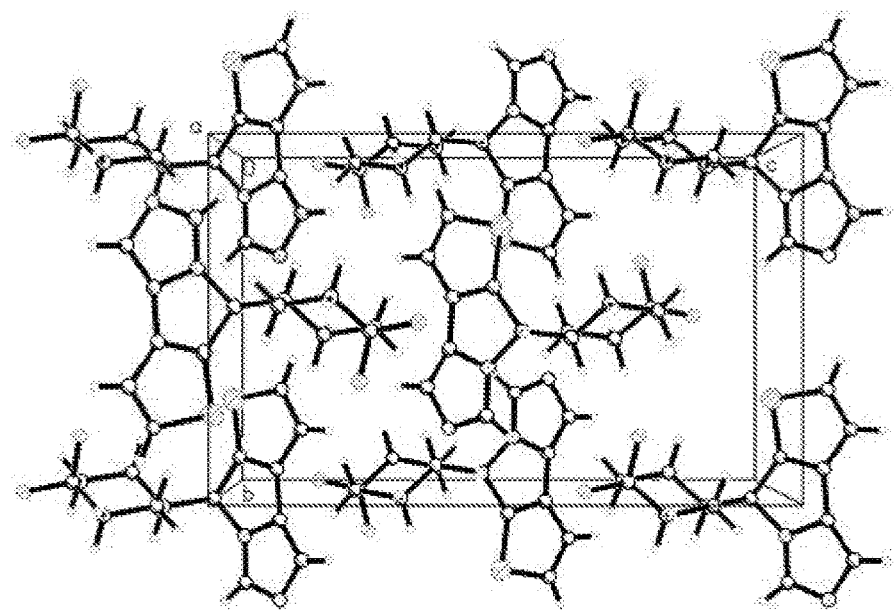
FIG. 3 is a cell packing diagram of the crystal of the compound of formula I along the a-axis direction.
Figure 4:
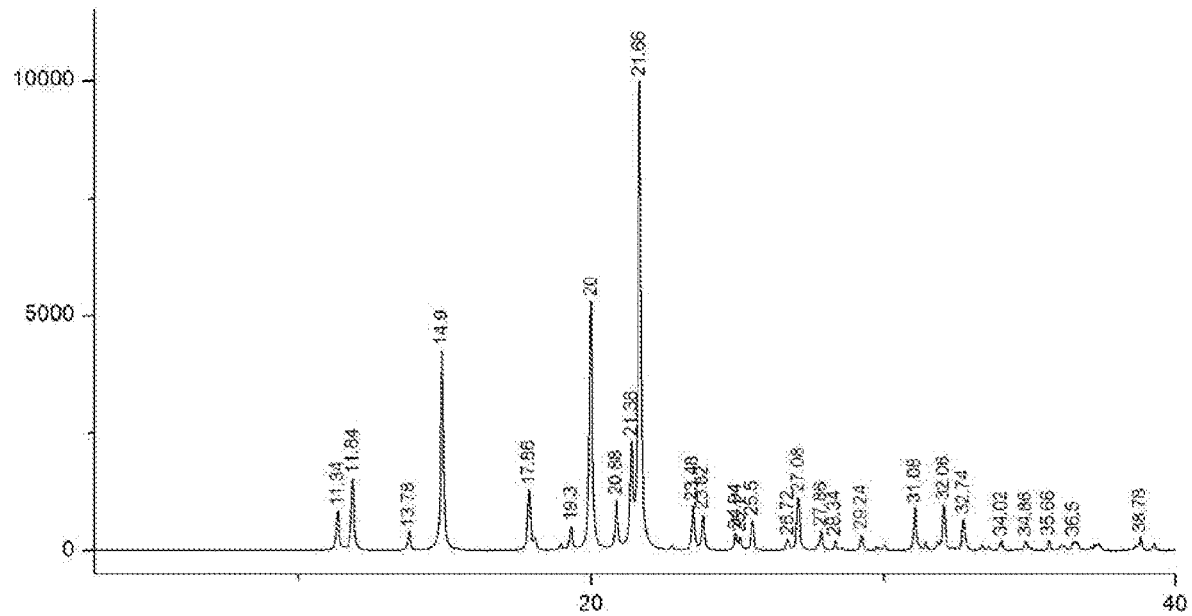
FIG. 4 is an X-ray powder diffraction pattern calculated from a single crystal of the crystal of the compound of formula I.

The following specific examples are intended to enable those skilled in the art to understand and implement the present application more clearly. They should not be considered as limits to the scope of this application, but are merely an exemplary illustration and typical representative of this application. Those skilled in the art will understand that there are other synthetic routes for forming the compounds of the present application, and the follows are provided as non-limiting examples.

All operations involving raw materials that are susceptible to oxidation or hydrolysis are performed under nitrogen protection. Unless otherwise stated, the raw materials used in this application are all commercially available and used without further purification. The solvents used in this application are all commercially available and used directly without special treatment. The compounds are named manually or via the ChemDraw® software, and the supplier's catalog names are adopted for the commercially available compounds.

The following abbreviations are used in the present application: DMF represents N,N-dimethylformamide; HATU represents O-(7-azabenzotriazol-1-yl)-N,N,N',N'-tetramethyluronium hexafluorophosphate; DIEA represents N,N-diisopropylethylamine; DIBAL-H represents diisobutylaluminum hydride; CDI represents carbonyldiimidazole; DMSO represents dimethyl sulfoxide.

Example 1: Preparation of the Compound of Formula I

A: 4,4-difluoro-N-methoxy-N-methyl-cyclohexanecarboxamide

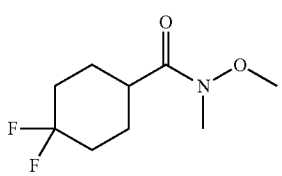

At 16° C., N-methoxymethylamine (653.42 mg, 6.70 mmol), HATU (2.55 g, 6.70 mmol) and DIEA (1.57 g, 12.18 mmol, 2.13 mL) were added into a solution of 4,4-difluorocyclohexanecarboxylic acid (1 g, 6.09 mmol) in DMF (10 mL), and the mixture was stirred for 16 hours. The reaction solution was dispersed in ethyl acetate (30 mL) and water (30 mL). The organic phase was separated out, washed with brine (30 mL×3), dried over anhydrous sodium sulfate, filtered and evaporated. The residue was purified by a silica gel column chromatography to give 1.2 g of the title compound.

$^1$H NMR (400 MHz, CHLOROFORM-d) δ=3.69 (s, 3H), 3.17 (s, 3H), 2.72 (brd, J=5.8 Hz, 1H), 2.22-2.09 (m, 2H), 1.87-1.77 (m, 5H), 1.76-1.65 (m, 1H).

B: 4,4-difluorocyclohexane carboxaldehyde

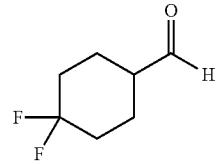

At −78° C., DIBAL-H (1 M, 12.74 mL) was slowly added into a solution of 4,4-difluoro-N-methoxy-N-methyl-cyclohexanecarboxamide (1.20 g, 5.79 mmol) in tetrahydrofuran (12.00 mL) under nitrogen protection. Then the reaction solution was stirred at −78° C. for 4 hours. The reaction solution was quenched with 1 N hydrochloric acid (5 mL), diluted with water (20 mL), and extracted with ethyl acetate (20 mL×3). The combined organic phases were washed with brine (20 mL×3), dried over anhydrous sodium sulfate, filtered and evaporated to give 780 mg of the title compound.

$^1$H NMR (400 MHz, CHLOROFORM-d) δ=9.66 (s, 1H), 2.39-2.28 (m, 1H), 2.07-1.98 (m, 4H), 1.84-1.73 (m, 4H).

C: (3-bromothien-2-yl)-(4,4-difluorocyclohexyl)methanol

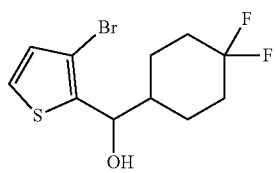 [SMILES: OC(c1sccc1Br)C1CCC(F)(F)CC1]

A solution of n-butyllithium (2.5 M, 2.29 mL) in diethyl ether (10.00 mL) was cooled to −78° C., and diisopropylamine (663.06 mg, 6.26 mmol) was slowly added thereto, and 3-bromothiophene (850 mg, 5.21 mmol) was added thereto 1 hour later, which was stirred for another 1 hour when being kept at −78° C. Then, 4,4-difluorocyclohexane carboxaldehyde (772.37 mg, 5.21 mmol) was added thereto, and the reaction system was stirred at −78° C. for 1 hour, which was quenched by adding ammonium chloride solution (30 mL), diluted with water (30 mL), and extracted with ethyl acetate (30 mL×3). The organic phase was washed with brine (30 mL×3), dried over anhydrous sodium sulfate, filtered and evaporated. The residue was purified by a silica gel column chromatography to give 700 mg of the title compound.

$^1$H NMR (400 MHz, CHLOROFORM-d) δ=7.30 (d, J=5.3 Hz, 1H), 6.94 (d, J=5.3 Hz, 1H), 4.86 (dd, J=2.4, 7.9 Hz, 1H), 2.29 (d, J=3.0 Hz, 1H), 2.19-2.07 (m, 3H), 1.82-1.63 (m, 4H), 1.52-1.46 (m, 2H).

D: 1-[(3-bromothien-2-yl)-(4,4-difluorocyclohexyl)methyl]-1H-imidazole

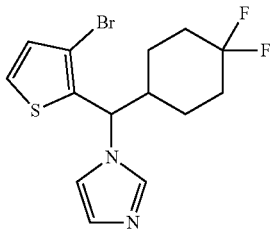 [SMILES: FC1(F)CCC(C(c2sccc2Br)n2ccnc2)CC1]

CDI (1.82 g, 11.25 mmol) was added into a solution of (3-bromothien-2-yl)-(4,4-difluorocyclohexyl)methanol (700 mg, 2.25 mmol) in acetonitrile (10 mL). The reaction system was stirred at 80° C. for 16 hours. The reaction solution was dispersed in ethyl acetate (20 mL) and water (20 mL). The organic phase was separated out, washed with brine (20 mL×3), dried over anhydrous sodium sulfate, filtered and evaporated. The residue was purified by a silica gel column chromatography to give 460 mg of the title compound.

MS-ESI (m/z): 361/363 (M+H)$^+$.

$^1$H NMR (400 MHz, CHLOROFORM-d) δ=7.65 (s, 1H), 7.34 (d, J=5.3 Hz, 1H), 7.08 (d, J=5.0 Hz, 2H), 6.95 (d, J=5.3 Hz, 1H), 5.28 (d, J=11.0 Hz, 1H), 2.21 (brd, J=11.5 Hz, 1H), 2.14-2.06 (m, 2H), 1.83-1.59 (m, 4H), 1.42-1.30 (m, 2H).

E: (S)-8-(4,4-difluorocyclohexyl)-8H-thieno[3,4]pyrrolo[1,5-a]imidazole (Compound of Formula I)

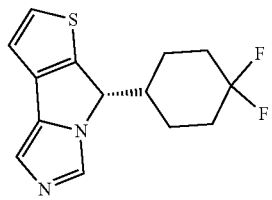 [SMILES: FC1(F)CCC([C@H]2c3sccc3-c3cncn32)CC1]

Under nitrogen protection, a solution of a mixture of 1-[(3-bromothien-2-yl)-(4,4-difluorocyclohexyl)methyl]-1H-imidazole (460 mg, 1.27 mmol), palladium acetate (28.51 mg, 127.00 μmol), tricyclohexyl phosphine (71.23 mg, 254.00 μmol), potassium carbonate (351.05 mg, 2.54 mmol) in o-xylene (5.00 mL) was stirred at 140° C. for 16 hours. The reaction solution was dispersed in ethyl acetate (20 mL) and water (20 mL). The organic phase was separated out, washed with brine (20 mL×3), dried over anhydrous sodium sulfate, filtered and evaporated. The residue was purified by a preparative silica gel column chromatography to give 190 mg of racemic 8-(4,4-difluorocyclohexyl)-8H-thieno[3,4]pyrrolo[1,5-a]imidazole.

MS-ESI (m/z): 281 (M+H)$^+$.

Racemic 8-(4,4-difluorocyclohexyl)-8H-thieno[3,4]pyrrolo[1,5-a]imidazole (190.00 mg, 677.75 μmol) was subjected to a chiral separation (chiral separation conditions: ChiralPak AD-3 150×4.6 mm I.D., 3 μm, mobile phase: A: carbon dioxide B: ethanol (0.05% diethylamine)) to give the title compound (53.00 mg, RT=4.619 min).

$^1$H NMR (400 MHz, METHANOL-d$_4$) δ=9.21 (s, 1H), 7.72 (d, J=5.0 Hz, 1H), 7.53 (s, 1H), 7.38 (d, J=5.0 Hz, 1H), 5.80 (d, J=3.8 Hz, 1H), 2.50 (dt, J=3.0, 12.2 Hz, 1H), 2.23-2.11 (m, 1H), 2.04-1.96 (m, 2H), 1.95-1.68 (m, 2H), 1.65-1.52 (m, 1H), 1.36-1.26 (m, 1H), 1.05 (dq, J=3.4, 13.1 Hz, 1H).

Example 2: Preparation of the Crystal of the Compound of Formula I 5.64 g of the compound of formula I prepared in Example 1 was dissolved in 180 mL of anhydrous ethanol. Until the solution was clarified, the insoluble substance was removed by filtration, and the filtrate was concentrated to obtain a solid-liquid mixture containing 35 mL of anhydrous ethanol. The solid-liquid mixture was heated to dissolve, and stirred under reflux for 1 hour. After stopping the heating, it was cooled down to room temperature with stirring to precipitate a solid. After filtration, the filter cake was dried under vacuum at 60° C. to give 4.34 g of the crystal of the compound of formula I.

Example 3: Cell Parameters of the Crystal of the Compound of Formula I

The crystallographic data and atomic coordinates and the like of the crystal of the compound of formula I are shown in Tables 2 and 3.

TABLE 2

| Crystal data and structure refinement | |
|---|---|
| Experimental molecular formula | $C_{14}H_{14}F_2N_2S$ |
| Molecular weight | 280.33 |
| Temperature | 296(2) K |
| Wavelength | 1.54178 Å |
| Crystal system | orthorhombic crystal system |
| Space group | P21 21 21 |
| Cell parameters | a = 8.5036(17) Å |
| | b = 9.809(2) Å |
| | c = 15.604(3) Å |
| | α = 90° |
| | β = 90° |
| | γ = 90° |
| Cell volume | 1301.6(5) Å$^3$ |
| Z | 4 |
| Calculated density | 1.431 mg/m$^3$ |
| Absorption correction parameter | 2.329 mm$^{-1}$ |
| F(000) | 584 |
| Crystal size | 0.16 × 0.12 × 0.10 mm |
| Data collection angle | 5.33° to 67.72° |
| Indicator collection range of hkl | −10 ≤ h ≤ 7, −11 ≤ k ≤ 11, −18 ≤ l ≤ 18 |
| Reflection data collection/independent | 6158/2301 [R(int) = 0.0319] |
| Data integrity of theta = 67.72 | 99.1% |
| Absorption correction method | Semiempirical equation |
| Maximum and minimum transmittances | 0.7530 and 0.5738 |
| Refinement method | F^2 full matrix least square method |
| Number of data/ Number of usage limitations/ Number of parameters | 2301/0/173 |
| F^2 fitting degree | 1.032 |
| Final R index [I > 2sigma(I)] | R1 = 0.0331, wR2 = 0.0820 |
| R index (all data) | R1 = 0.0369, wR2 = 0.0850 |
| Absolute configuration parameters | 0.05(2) |
| Extinction coefficient | 0.0080(7) |
| Maximum difference Peak and valley | 0.161 and −0.180 e. Å$^{-3}$ |

TABLE 3

Atomic coordinates (×10⁴) and equivalent isotropic displacement parameters ($Å^2 \times 10^3$)

| Atom | X | Y | Z | U(eq) |
|---|---|---|---|---|
| S(1) | 8395(1) | 7625(1) | 9962(1) | 61(1) |
| F(1) | 11043(2) | 6653(1) | 12565(1) | 74(1) |
| F(2) | 11244(2) | 5083(2) | 13539(1) | 83(1) |
| N(1) | 8806(2) | 3616(2) | 9736(1) | 47(1) |
| N(2) | 9767(3) | 1849(2) | 9042(1) | 64(1) |
| C(1) | 8176(2) | 4661(2) | 10334(1) | 45(1) |
| C(2) | 8663(2) | 5912(2) | 9834(1) | 48(1) |
| C(3) | 9425(3) | 7945(3) | 9029(2) | 64(1) |
| C(4) | 9934(3) | 6801(3) | 8647(1) | 59(1) |
| C(5) | 9496(2) | 5620(2) | 9111(1) | 48(1) |
| C(6) | 9622(3) | 4145(2) | 9049(1) | 48(1) |
| C(7) | 10205(3) | 3033(3) | 8627(2) | 60(1) |
| C(8) | 8941(3) | 2252(2) | 9710(2) | 57(1) |
| C(9) | 8898(2) | 4481(2) | 11228(1) | 43(1) |
| C(10) | 8154(3) | 5432(2) | 11879(1) | 53(1) |
| C(11) | 8870(3) | 5224(2) | 12770(1) | 57(1) |
| C(12) | 10629(3) | 5324(2) | 12739(1) | 53(1) |
| C(13) | 11397(3) | 4422(2) | 12098(1) | 52(1) |
| C(14) | 10683(2) | 4638(2) | 11213(1) | 50(1) |
| H(1A) | 7028 | 4600 | 10365 | 54 |
| H(3A) | 9607 | 8816 | 8815 | 77 |
| H(4A) | 10505 | 6787 | 8139 | 70 |
| H(7A) | 10809 | 3068 | 8131 | 72 |
| H(8A) | 8505 | 1665 | 10113 | 68 |
| H(9A) | 8670 | 3546 | 11412 | 52 |
| H(10A) | 7031 | 5263 | 11903 | 63 |
| H(10B) | 8311 | 6369 | 11700 | 63 |
| H(11A) | 8461 | 5910 | 13158 | 69 |
| H(11B) | 8569 | 4336 | 12988 | 69 |
| H(13A) | 11265 | 3477 | 12268 | 62 |
| H(13B) | 12515 | 4617 | 12079 | 62 |
| H(14A) | 11128 | 3982 | 10817 | 60 |
| H(14B) | 10950 | 5544 | 11010 | 60 |

Example 4: Single Crystal Calculated X-ray Powder Diffraction Data of the Crystal of the Compound of Formula I 1. Calculation software: Mercury 3.8 (Build RC2); wavelength: 1.54056 Å.
2. X-ray powder diffraction data
The peak positions and intensities of the characteristic peaks in the X-ray powder diffraction spectrum calculated from the single crystal of the crystal of the compound of formula I are shown in Table 4.

TABLE 4

| No. | 2θ (degree) | relative intensity (I/I₀) |
|---|---|---|
| 1 | 11.34 | 8.6 |
| 2 | 11.84 | 12.1 |
| 3 | 13.78 | 4.2 |
| 4 | 14.90 | 38.3 |
| 5 | 17.86 | 14.1 |
| 6 | 19.30 | 4.4 |
| 7 | 20.00 | 53.0 |
| 8 | 20.88 | 9.8 |
| 9 | 21.38 | 22.8 |
| 10 | 21.66 | 100.0 |
| 11 | 23.48 | 6.0 |
| 12 | 23.82 | 4.8 |
| 13 | 24.94 | 3.2 |
| 14 | 25.10 | 2.8 |
| 15 | 25.50 | 4.0 |
| 16 | 26.72 | 2.2 |
| 17 | 27.08 | 12.1 |
| 18 | 27.86 | 4.0 |
| 19 | 28.34 | 1.9 |
| 20 | 29.24 | 3.7 |
| 21 | 31.08 | 10.0 |
| 22 | 32.06 | 6.3 |
| 23 | 32.74 | 6.0 |
| 24 | 34.02 | 2.3 |
| 25 | 34.86 | 1.3 |
| 26 | 35.66 | 1.7 |
| 27 | 36.50 | 2.2 |
| 28 | 38.78 | 1.9 |

Experimental Example 1: In Vitro hIDO1 Enzyme Activity Test

1. Experimental Objective

The change of NFK production was detected by using the NFK Green™ fluorescent molecule, which is the metabolite of the IDO1 enzyme, and the $IC_{50}$ value of the compound was used as an index, to evaluate the inhibitory effect of the compound of formula I on the recombinant human IDO1 enzyme.

2. Experimental Materials
IDO1 Enzyme Activity Assay Kit, NTRC #NTRC-hIDO-10K;
384-well enzyme reaction plate, PerkinElmer #6007279;
384-well compound plate, Greiner #781280;
Microplate sealing film, PerkinElmer #6050185;
Envision Multimode Microplate Reader, PerkinElmer;
Bravo automated liquid handling platform, Agilent.

3. Experiment Steps and Methods
1) Compound Loading
The compound of formula I was diluted to 1 mM with DMSO, and then diluted 3-fold in duplicate wells, with 10 gradients. 48 μL of 50 mM phosphate buffer (pH 6.5) was transferred and added to the compound plate via Bravo automated liquid handling platform. 2 μL of the diluted solution of the compound in DMSO was then added thereto and mixed, followed by transferring 10 μL thereof to an enzyme reaction plate.

2) IDO1 Enzyme Activity Assay
The IDO1 enzyme was diluted to 20 nM in the reaction buffer (50 mM phosphate buffer (pH 6.5), 0.1% Tween-20, 2% glycerol, 20 mM ascorbic acid, 20 μg/mL catalase and 20 μM methylene blue), 20 μL of which was transferred to an enzyme reaction plate and incubated at 23° C. for 30 min. The reaction was started by adding 10 μL of 400 μM L-tryptophan substrate and incubated at 23° C. for 90 min. 10 μL of NFK Green™ fluorescent dye was added thereto, and the plate was sealed with the microplate sealing film, incubated at 37° C. for 4 h, and then read on Envision Multimode Microplate Reader (Ex 400 nm/Em 510 nm).

3) Data Analysis
The reference wells having the IDO1 enzyme but without compound of formula I were set as 0% inhibition rate, and the reference wells without the IDO1 enzyme were set as 100% inhibition rate, and the $IC_{50}$ value of the compound was calculated by analyzing the data with XLFit 5.

Experimental Example 2: hIDO1 Cytological Activity Assay

1. Experimental Objective
The change of kynurenine in Hela cells was detected by the LC-MS method, and the $IC_{50}$ value of the compound was used as an index to evaluate the inhibitory effect of the compound of formula I on IDO1 enzyme.

2. Experimental Materials

Cell line: Hela cells;

Culture medium: RPMI 1640 phenol red free, Invitrogen #11835030

10% fetal bovine serum, Gibco #10099141

1× Penicillin-Streptomycin, Gibco #15140-122;

Precipitant: 4 μM L-kynurenine-d4 dissolved in 100% acetonitrile, CacheSyn #CSTK008002;

Trypsin, Invitrogen #25200-072;

DPBS, Hyclone #SH30028.01B;

Recombinant human γ-interferon, Invitrogen #PHC4033;

5% (w/v) trichloroacetic acid, Alfa Aesar #A11156;

96-well cell plate, Corning #3357;

96-well compound plate, Greiner #781280;

96-well V-bottom plate, Axygen #WIPP02280;

$CO_2$ incubator, Thermo #371;

Centrifuge, Eppendorf #5810R;

Vi-cell cell counter, Beckman Coulter;

Labcyte FLIPR, Molecular Device.

3. Experiment Steps and Methods

1) Hela Cell Inoculation

The culture medium, trypsin and DPBS were preheated in a 37° C. water bath. The culture medium for cell culture was sucked out and washed with 10 mL of DPBS; the preheated trypsin was added into the culture flask, and the flask was rotated to allow the trypsin to uniformly cover it, and then placed in a 37° C., 5% $CO_2$ incubator to digest for 1-2 min; in each T150, cells were dispersed with 10-15 mL of the culture medium, centrifuged at 800 rpm for 5 min, and then resuspended with 10 mL of medium; 1 mL of cell suspension was pipetted and cells were counted with Vi-cell; Hela cells were diluted with the culture medium to $5×10^5$/mL, 80 μL of the solution was added to a 96-cell plate, and cultured at 37° C. for 5-6 h in a 5% $CO_2$ incubator.

2) Compound Loading

The compound was diluted to 1 mM with DMSO, and then diluted 3-fold in duplicate wells, with 9 gradients. 5 μL of the diluted solution of the compound in DMSO was added to the compound plate containing 95 μL of the culture medium, and mixed, followed by transferring 10 μL thereof to a cell plate.

3) Cytological Activity Assay

10 μL of recombinant human γ-interferon was added to a final concentration of 100 ng/mL to induce IDO1 expression. The cells were incubated at 37° C. for 20 h in a 5% $CO_2$ incubator. 4 μL of 5% (w/v) trichloroacetic acid was added thereto, mixed and incubated at 50° C. for 30 min. After centrifugation at 2400 rpm for 10 min, 40 μL of the supernatant was taken and placed in a 96-well V-bottom plate, and then a precipitant was added thereto. After mixing, it was centrifuged at 4000 rpm for 10 min. 100 μL of the supernatant was transferred to a new 96-well V-bottom plate. The content of kynurenine was detected by LC-MS.

4) Data Analysis

The reference wells having γ-interferon but without compound of formula I were set as 0% inhibition rate, and the reference wells without Hela cell were set as 100% inhibition rate, and the $IC_{50}$ value of the compound of formula I was calculated by analyzing the data with XLFit 5.

The experimental results were found in Table 5.

TABLE 5

IC$_{50}$ test results of hIDO1 enzyme activity in vitro

| Tested sample | hIDO1 | |
| --- | --- | --- |
| | Enzyme activity (nM) | Cytological active (nM) |
| Compound of formula I | 48.05 | 74.93 |

What is claimed is:

1. A crystal of (S)-8-(4,4-difluorocyclohexyl)-8H-thieno[3,4]pyrrolo[1,5-a]imidazole represented by formula I,

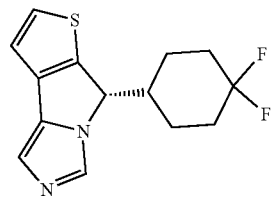 [SMILES: FC1(F)CCC([C@H]2c3sccc3-c3cncn32)CC1]

wherein an X-ray powder diffraction spectrum thereof has diffraction peaks expressed by 2θ values at 11.49±0.2°, 11.99±0.2°, 15.05±0.2°, 20.14±0.2°, 21.53±0.2° or 21.79±0.2°.

2. The crystal according to claim 1, wherein the X-ray powder diffraction spectrum thereof has diffraction peaks expressed by 2θ values at 11.49±0.2°, 11.99±0.2°, 15.05±0.2°, 17.99±0.2°, 18.24±0.2°, 19.44±0.2°, 20.14±0.2°, 21.53±0.2°, 21.79±0.2°, 25.09±0.2°, 27.20±0.2° or 28.00±0.2°.

3. The crystal according to claim 2, wherein the X-ray powder diffraction spectrum thereof has diffraction peaks expressed by 2θ values at 11.49±0.2°, 11.99±0.2°, 15.05±0.2°, 17.99±0.2°, 18.24±0.2°, 19.44±0.2°, 20.14±0.2°, 21.53±0.2°, 21.79±0.2°, 23.64±0.2°, 23.98±0.2°, 25.09±0.2°, 27.20±0.2°, 28.00±0.2°, 29.35±0.2°, 31.22±0.2°, 32.01±0.2°, 32.21±0.2°, 36.70±0.2° or 38.87±0.2°.

4. The crystal according to claim 3, wherein the X-ray powder diffraction spectrum thereof has diffraction peaks expressed by 2θ values at 11.49±0.2°, 11.99±0.2°, 13.89±0.2°, 15.05±0.2°, 17.99±0.2°, 18.24±0.2°, 19.44±0.2°, 20.14±0.2°, 21.02±0.2°, 21.53±0.2°, 21.79±0.2°, 23.64±0.2°, 23.98±0.2°, 25.09±0.2°, 25.64±0.2°, 26.84±0.2°, 27.20±0.2°, 28.00±0.2°, 28.46±0.2°, 29.35±0.2°, 31.22±0.2°, 32.01±0.2°, 32.21±0.2°, 32.89±0.2°, 34.18±0.2°, 35.02±0.2°, 35.81±0.2°, 36.70±0.2° or 38.87±0.2°.

5. The crystal according to claim 1, wherein the differential scanning calorimetry diagram has an absorption peak at 207±5° C.

6. A crystal composition, wherein the crystal according to claim 1 accounts for 50% or more by weight of the crystal composition.

7. A pharmaceutical composition, comprising the crystal according to claim 1 or the crystal composition according to claim 6.

8. The crystal composition according to claim 6, wherein the crystal accounts for 80% or more by weight of the crystal composition.

9. The crystal composition according to claim 8, wherein the crystal accounts for 90% or more by weight of the crystal composition.

10. The crystal composition according to claim 9, wherein the crystal accounts for 95% or more by weight of the crystal composition.

11. A method for treating indoleamine 2,3-dioxygenase-mediated immunosuppressive disease in a subject in need thereof comprising administering the crystal according to claim 1.

12. A method for preparing the crystal according to claim 1, comprising: (1) dissolving the compound of formula I in an organic solvent until solution being clear, which is filtered to remove insoluble substance; (2) concentrating filtrate obtained in step (1) to a solid-liquid mixed state, producing a solid-liquid mixture which is dissolved by heating, stirred with refluxing for 1 to 2 hours, and cooled for crystallization.

13. The method according to claim 12, wherein the organic solvent in step (1) is one solvent or a mixed solvent selected from methanol, ethanol, acetonitrile, acetone, butanone, tetrahydrofuran, and 1,4-dioxane.

14. The method according to claim 12, wherein a molar volume ratio of the compound of formula I to the organic solvent in step (1) is 1 mmol:5-10 mL.

15. The method according to claim 12, wherein, in step (2), when the filtrate is concentrated to a solid-liquid mixed state, a volume of the organic solvent in the solid-liquid mixture accounts for 15% to 30% of a total volume of the organic solvent in step (1).

16. The method according to claim 12, wherein a temperature of the refluxing in step (2) is 50° C. to 80° C.

17. The method according to claim 12, wherein a temperature of cooling for crystallization in step (2) is 20° C. to 30° C.

18. The method according to claim 12, further comprising: (3) filtering; and (4) drying.

19. The method according to claim 12, wherein the organic solvent in step (1) is methanol or ethanol.

20. The method according to claim 12, wherein a molar volume ratio of the compound of formula I to the organic solvent step (1) is 1 mmol:8-10 mL.

* * * * *